United States Patent
Lang et al.

(10) Patent No.: US 7,662,167 B2
(45) Date of Patent: Feb. 16, 2010

(54) MEDICAL INSTRUMENT

(75) Inventors: Dieter Lang, Stockheim (DE); Thomas Hopf, Stockheim (DE)

(73) Assignee: Karl Storz GmbH & Co. KG (DE)

( * ) Notice: Subject to any disclaimer, the term of this patent is extended or adjusted under 35 U.S.C. 154(b) by 664 days.

(21) Appl. No.: 10/626,414

(22) Filed: Jul. 24, 2003

(65) Prior Publication Data
US 2004/0220601 A1    Nov. 4, 2004

Related U.S. Application Data

(63) Continuation of application No. PCT/EP03/01303, filed on Feb. 11, 2003.

(30) Foreign Application Priority Data

Feb. 21, 2001   (DE)   ................. 102 07 207

(51) Int. Cl.
*A61B 17/28*   (2006.01)
*A61B 17/32*   (2006.01)
(52) U.S. Cl. ....................... 606/205; 606/207
(58) Field of Classification Search .......... 606/205, 606/206, 207, 208, 167, 170, 174
See application file for complete search history.

(56) References Cited

U.S. PATENT DOCUMENTS

| 4,712,545 | A |   | 12/1987 | Honkanen |
| 4,994,024 | A |   | 2/1991 | Falk |
| 5,478,351 | A |   | 12/1995 | Meade et al. |
| 5,490,861 | A |   | 2/1996 | Kratsch et al. |
| 5,613,977 | A |   | 3/1997 | Weber et al. |
| 6,270,508 | B1 | * | 8/2001 | Klieman et al. ............. 606/147 |

FOREIGN PATENT DOCUMENTS

| DE | 35 26 822 A1 | 2/1987 |
| DE | 38 02 907 A1 | 8/1989 |
| DE | 94 18 094.6 | 1/1995 |
| DE | 93 20 869.3 | 3/1995 |
| DE | 197 13 067 A1 | 10/1998 |
| DE | 199 15 427 A1 | 10/2000 |
| DE | 199 30 426 A1 | 1/2001 |

* cited by examiner

*Primary Examiner*—Vy Q Bui
(74) *Attorney, Agent, or Firm*—St. Onge Steward Johnston & Reens LLC

(57) ABSTRACT

The invention relates to a medical instrument with a hollow shaft, a handle, and a tool, where at least one jaw member of the tool can be rotated in relation to the at least one other jaw member of the tool for purposes of opening and closing by means of one rotatably configured gripping member of the handle, and the rotatable jaw member and the gripping member of the handle that serves to rotate are connected to one another by means of a push pin installed in the hollow shaft. To create a simple construction ensuring the best possible power transmission along with a good cutting sensation for the operator, a rigid casing can be inserted into the push pin, at least partly in form-locking connection, which casing in turn can be inserted, at least partly in form-locking connection, into the hollow shaft and the push pin is mounted in the casing so that it is at least partly rotation-resistant.

12 Claims, 5 Drawing Sheets

MEDICAL INSTRUMENT

This application is a continuation of pending International Patent Application No. PCT/EP03/01303 filed Feb. 11, 2003 which designates the United States and claims priority of pending German Application No. 102 07 207.8 filed Feb. 21, 2002.

FIELD OF THE INVENTION

The invention relates to a medical instrument with a hollow shaft having at its proximal end a handle consisting of at least two gripping members and at its distal end a tool consisting of at least two jaw members, where at least one of the jaw members of the tool can be rotated in relation to the at least one other jaw member of the tool for purposes of opening and closing by means of one rotatably shaped gripping member of the handle, and the at least one rotatable jaw member and the gripping member of the handle that serves to rotate the at least one jaw member are connected to one another by means of a push pin installed in the hollow shaft and the push pin can be displaced exclusively in the axial direction by means of the related at least one rotatable gripping member of the handle.

Conventional instruments couple the movable jaw member or the movable jaw members starting from the push pin by means of a lever mechanism. The angle between the instrument's axis and the line through the pivot point of the jaw member and of the contact point on the lever is selected to be as wide as possible. In opening or closing the jaw members, the angle is inevitably reduced, however, and thus the transmission of power is clearly worsened. Because of the coupling of the push pin to the adjustable gripping member of the handle, which coupling causes the proximal end of the push pin to move in an arc like a circle segment, the push pin requires some vertical play inside the hollow shaft. This vertical play, however, involves the risk of tilting and/or twisting the push pin inside the hollow shaft, so that the operator's direct cutting sensation may be strongly reduced.

A conventional medical instrument is known from U.S. Pat. No. 5,490,861A. In this medical instrument the push pin is operated along the axis by means of a tooth system configured both on the rotatable gripping member and also on the proximal end of the push pin. Upon actuating the rotatable gripping member, the latter's teeth engage with the corresponding tooth system of the push pin and displaces this pin exclusively in the axial direction.

In addition to the entirely axial operation of the push pin, however, the rotation-proof installation of the push pin, which is intended to safeguard this rod against torsion, is critical to perfect power transmission to the instrument and to a good, secure cutting sensation on the operator's part. This requisite resistance to torsion is not found in the medical instrument known from U.S. Pat. No. 5,490,861A, because the cylindrical push pin is installed in a shaft with cylindrical channel cross-section for the push pin, and therefore the push pin can rotate freely inside the shaft. Even the helical spring on the distal end of the push pin does not ensure the desired security against rotation, but rather this spring, which is costly to install, weakens the operator's cutting sensation, because the spring absorbs part of the torque power and thus makes it impossible for the operator to adjust the cutting power of the tool by means of the actuator of the gripping member.

Another medical instrument is known from U.S. Pat. No. 4,712,545A. In this familiar surgical instrument the spherical thickened proximal end of the push pin is installed in the movable gripping member of the handle in such a way that the proximal end of the push pin is moved along an arc around the rotation axis of the movable gripping member. Because of this motion and the corresponding required vertical play, the push pin can easily be tilted inside the shaft. In addition, the movable jaw member is installed in the stationary portion of the shaft in that is slides on a curved trajectory as a slide bearing. This configuration leads to imaginary pivot points that lie partly outside the instrument's shaft. As a result, however, only the lever arm is enlarged—similar effects can be achieved by such methods on the handle—and thus in every position more power is transmitted. However, the smaller the angle between the line connecting the jaw member rotation point, the push pin pressure point, and the instrumental axis, the smaller is the jaw member closing power.

On the basis of this state of the art, the object of the invention is, with a simple construction of the medical instrument, to install the push pin so that at least sections of it are rotation-resistant in the hollow shaft, in order to ensure the best possible power transmission along with a good cutting sensation for the operator.

This object is achieved by means of the invention in that the push pin can be inserted, secured at least partly in form-locking connection, into a rigid casing, which in turn can be inserted, at least in some sections form-locking, into the hollow shaft and the push pin can be installed in the casing, with at least sections of it being rotation-resistant.

By installing a casing in the hollow shaft to receive the push pin, it is possible by means of simple construction means to install the push pin so that it resists rotation inside the shaft, because this requires no constructive modification of the shaft, but instead the casing that is to be inserted into the hollow shaft must be configured in such a way that it prevents torsion of the push pin, for instance by shaping the cross-section to match the push pin. It is advantageous that the push pin is installed in the casing, moreover, so that it resists rotation at least in sections.

In addition, the design also makes it possible later to retrofit a hollow shaft of greater diameter in such a way as to ensure that the push pin that is installed so that it is airtight and resists rotation.

Because the push pin is displaced entirely along the axis, it is possible to configure the medical instrument in such a way that the push pin enters the hollow shaft without free play.

In a practical embodiment of the invention, it is further proposed that the casing should include, for instance, a recess with a rectilinear cross-section for receiving the push pin which is rectilinear in cross-section.

To configure a purely axial displacement of the push pin in the distal direction, a pressure surface for contacting a contact surface of the push pin is configured on the rotatable gripping member in such a way that the rotatable gripping member presses the push pin in an exact straight line in the distal direction. To displace the push pin in the proximal direction, a driving element is mounted on the rotatable gripping member and said receiver element engages in a recess formed in the push pin and thus pulls the push pin back in an exact straight line in proximal direction without vertical or lateral divergent motion.

Finally, it is proposed with the present invention that the diameter of the casing should correspond at least to the maximum height of the push pin, so that the push pin can be withdrawn from the hollow shaft after releasing the tool together with the casing at the proximal end to allow better cleansing and to facilitate installation and repair.

BRIEF DESCRIPTION OF DRAWINGS

Other features and advantages of the invention derive from the following description of the associated illustrations, in which one embodiment of an inventive medical instrument is presented by way of example. The illustrations are as follows.

DETAILED DESCRIPTION OF DRAWINGS

Figure 1:
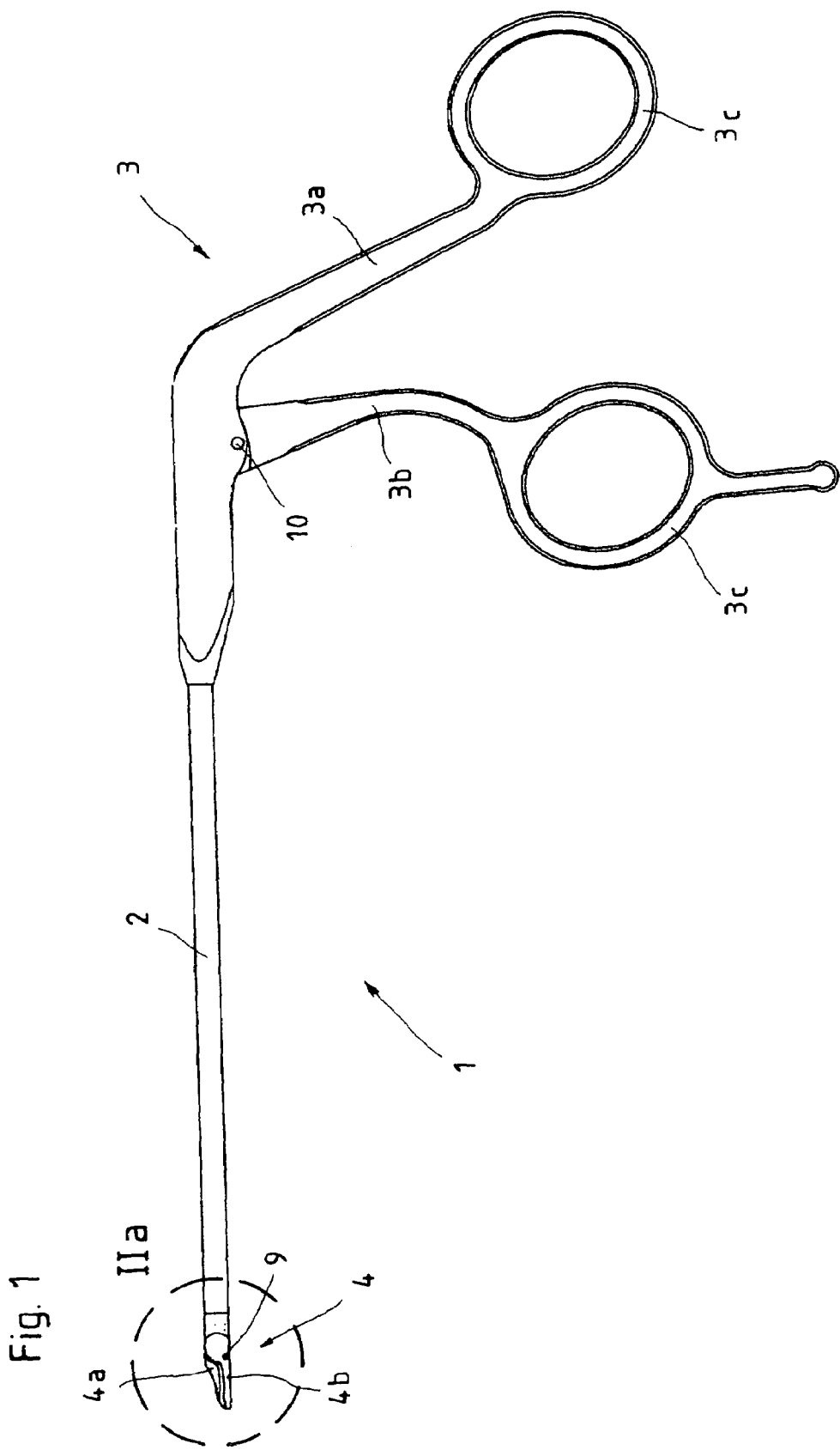
FIG. 1 is a lateral view of an inventive medical instrument showing the jaw members in the closed position.

The illustration in FIG. 1 shows a lateral view of a medical instrument 1, whose power transmission mechanism can be used in various ways, for instance for punching, cutting, holding a needle, as gripping instruments, and the like.

The medical instrument 1 consists essentially of a hollow shaft 2 on whose proximal end a handle 3 is mounted, which consists of a stationary gripping member 3a and a gripping member 3b that is rotatable in relation to the stationary gripping member 3a. At the distal end of the shaft 2, a tool 4 is mounted, which in the embodiment in the illustration has a rotatable jaw member 4a and a jaw member 4b that is rigidly connected with the shaft 2.

Figure 2A:
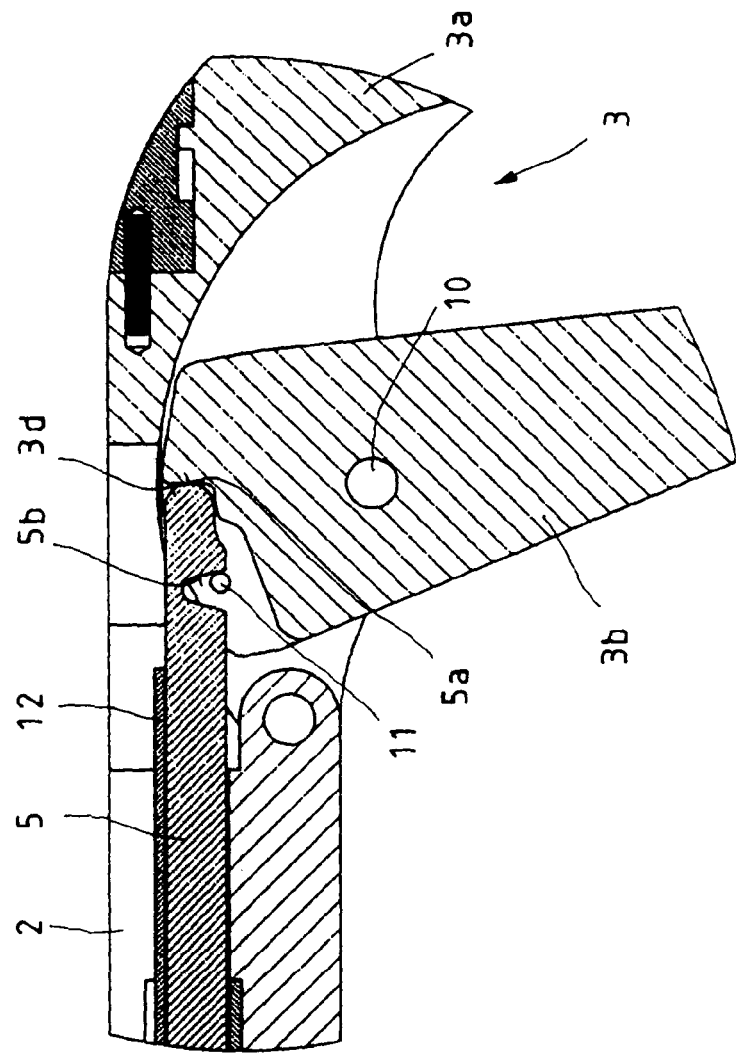
FIG. 2a is an enlarged partial longitudinal view through the medical instrument according to FIG. 1.
Figure 2A:
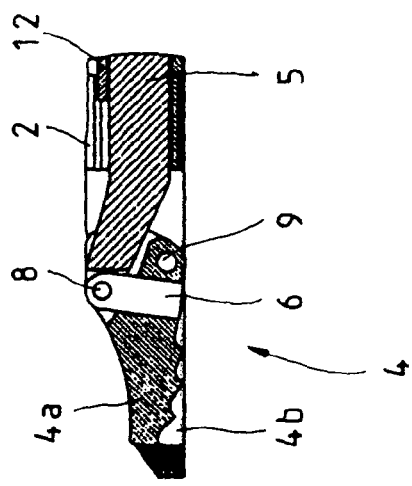
Figure 2B:
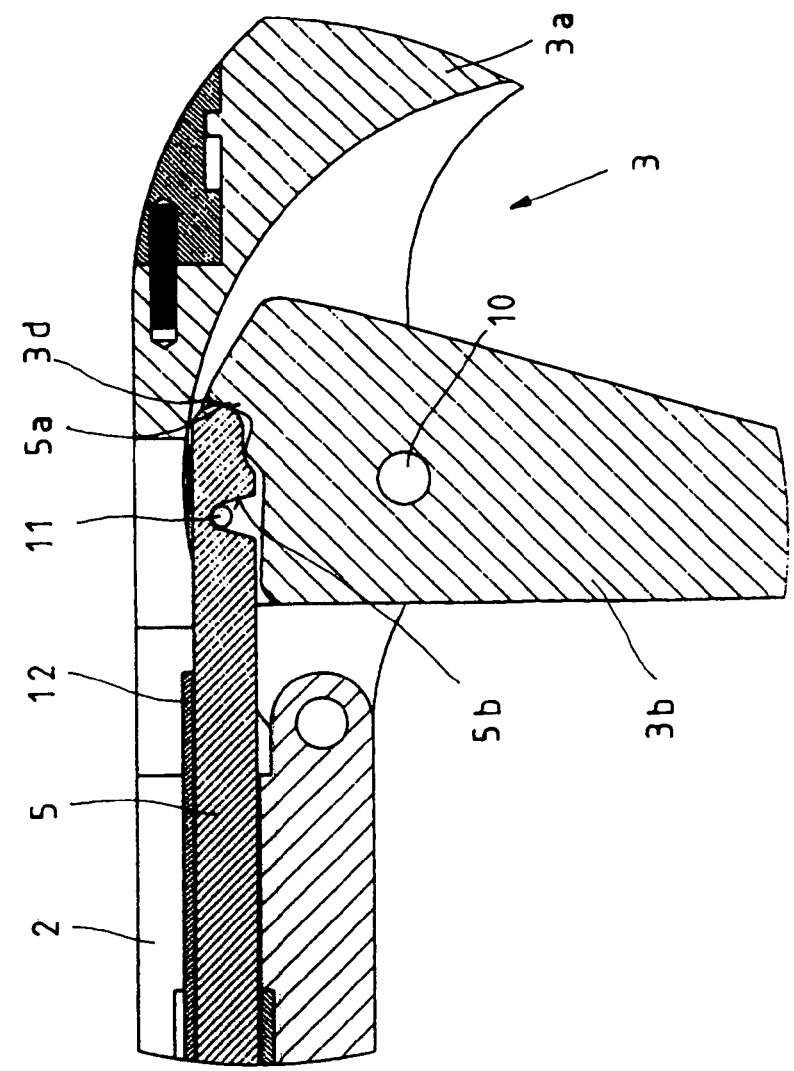
FIG. 2b is a view according to FIG. 2a but showing the jaw members in open position.
Figure 2B:
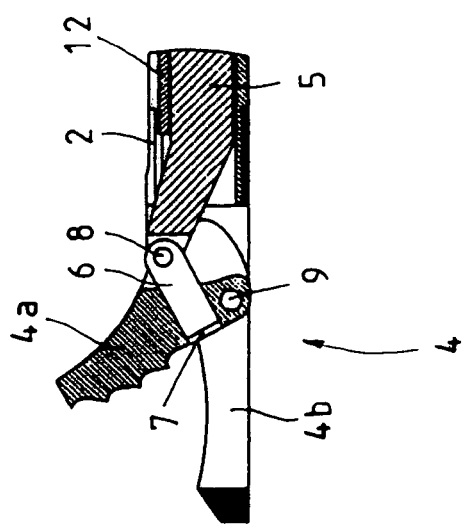

As can be seen from the detail views in FIGS. 2a and 2b, the rotatable jaw member 4a of the tool 4 and the rotatable gripping member 3b of the handle 3 are connected with one another by means of a push pin 5, mounted in the hollow shaft 2, in such a manner that the adjustable jaw member 4a can be moved from the closed position (FIGS. 1 and 2a) into the open position (FIG. 2b) or vice versa by rotation of the gripping member 3b.

To achieve the best possible power transmission between the handle 3 and the adjustable jaw member 4a of the tool 4, the push pin 5 and the rotatable jaw member 4a are connected with one another, as shown for instance in FIG. 2b, by means of a compensation lever 6 whereby the compensation lever 6 is mounted so that it can slide in a guide groove 7 configured in the rotatable jaw member 4a, and a contact point 8 between the compensation lever 6 and the push pin 5 is mounted above a rotation point 9 of the rotatable jaw member 4a. It is also possible, of course, to configure the medical instrument in such a way that the push pin 5 directly contacts the rotatable jaw member 4a.

The connection of the push pin 5 and the rotatable jaw member 4a by means of the compensation lever 6 that can slide in the jaw member 4a allows a stable lever ratio between the two components 5 and 4a, without the risk of a swinging motion of the push pin 5. Because of this stable lever ratio, the operator maintains a good, uniform cutting sensation.

To ensure firm action of the gripping members 3a, 3b of the handle 3, these members have finger loops 3c on their free ends. In the illustrated embodiment, the gripping member 3b is rotatable around a rotation axis 10 in relation to the other, stationary gripping member 3a. The rotation path of the two gripping members 3a, 3b toward one another can be shortened by means of a transmission that is not shown in the illustration. It is also possible to configure both gripping members 3a, 3b of the handle 3 as rotatable gripping members. As a result of the coupling of the rotatable handle member 3b by the push pin 5 and the compensation lever 6 with the rotatable jaw member 4a the tool 4 can be opened and closed by actuating the handle 3.

The push pin 5 is operated in such a way that it can be displaced entirely axially inside the hollow shaft 2 in order to actuate the rotatable jaw member 4a. As can be seen from a comparison of FIGS. 2a and 2b, the push pin 5 is pushed in the distal direction by the rotatable handle member 3b to close the rotatable jaw member 4a. For this purpose, on the rotatable handle member 3b a pressure surface 3d is configured and acts, together with a corresponding contact surface 5a, upon the push pin 5. Contrary to the state of current technology, in which the proximal end of the push pin 5 has a spherical bearing head, which is stored in a corresponding bearing recess of the rotatable gripping member 3b, resulting in a movement of the proximal end of the push pin 5 on a circle-segment-shaped path, it is possible, through the configuration of the pressure surface 3d on the rotatable gripping member 3b on the one hand, and of the contact surface 5a on the push pin 5 on the other hand, to reduce the movement of the push pin 5 to a strictly axial motion.

The push pin 6 is retracted in proximal direction to move the rotatable jaw member 4a from the closed position illustrated in FIG. 2a into the open position as in FIG. 2b by means of a driving element 11, mounted on the rotatable gripping member 3b, which element engages with a recess 5b formed in the push pin 5. This strictly pushing/pulling motion also causes a movement of the push pin 5 exclusively in the axial direction.

Figure 3A:
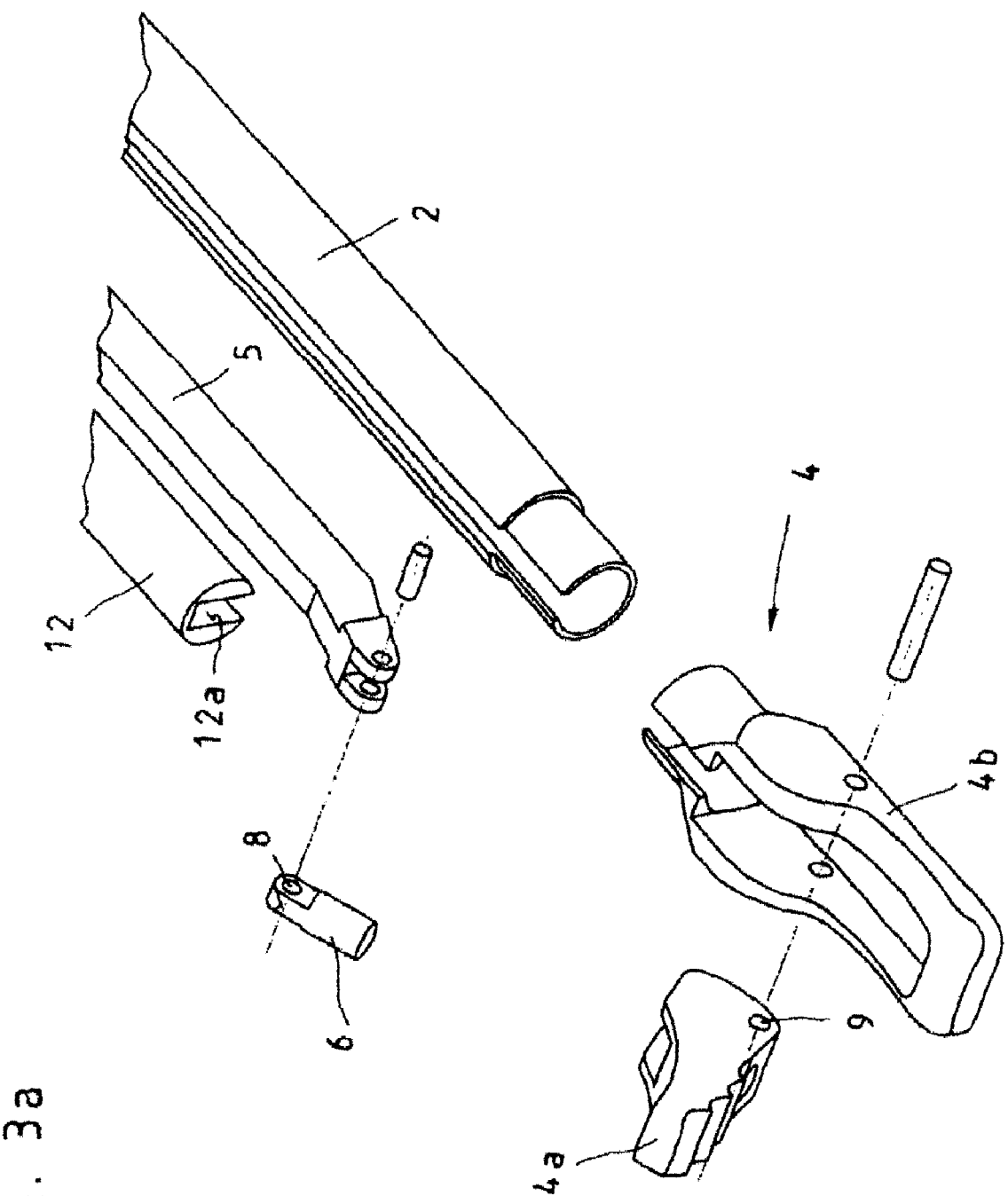
FIG. 3a is an exploded view of the distal end of the medical instrument according to FIG. 1.
Figure 3B:
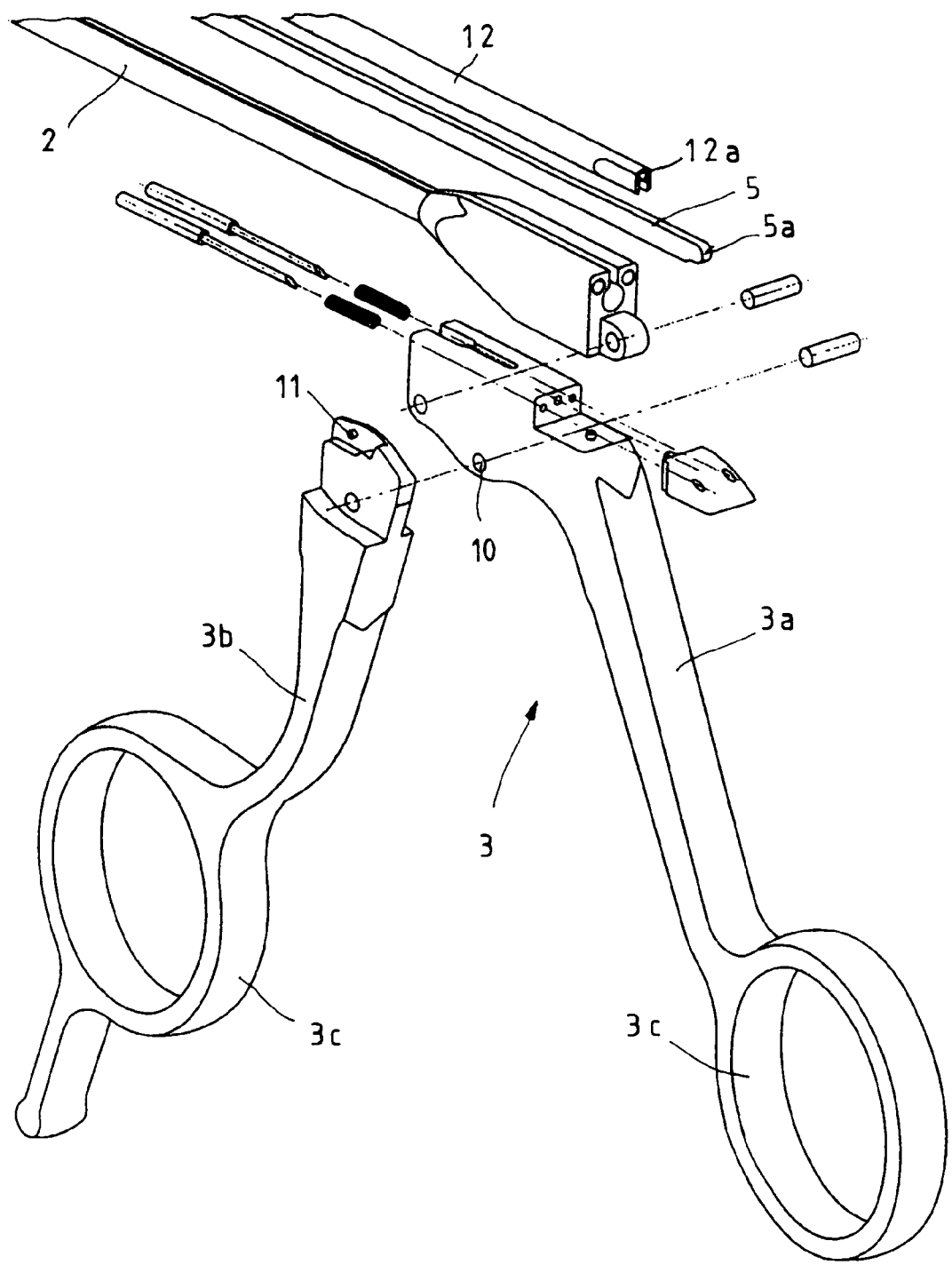
FIG. 3b is an exploded view of the proximal end of the medical instrument according to FIG. 1.

Because, owing to the strictly axial movement of the push pin 5, no swinging motion of the push pin 5 occurs, it is possible to mount the push pin 5 without play in the hollow shaft 2. For this purpose a casing 12 is provided, into which the push pin 5 can be inserted, at least partly in form-locking connection, so that the casing 12 in turn can be inserted, at least partly in form-locking connection, into the hollow shaft 2, as can be seen from the explosion illustrations in FIGS. 3a and 3b.

To further ensure that the push pin 5 can also be moved torsion-free, that is, resistant to rotation inside the shaft 2, in the illustrated embodiment a recess 12a is configured for receiving the push pin 5 in the casing 12 in such a way that the inner contour of the recess 12a is rectilinear in shape, corresponding in shape to the outer contour of the likewise rectilinear push pin 5. The use of the casing 12 offers the possibility of ensuring motion of the push pin 5 inside the shaft 2 without play even when the inner diameter of the hollow shaft 2 differs from the outer diameter of the push pin 5. In addition, by configuring the push pin 5 with rectilinear cross-section, the individual components become far easier to produce.

To facilitate cleaning and repair of the medical instrument 1, the push pin 5 and the compensation lever 6 can be removed as a complete unit from the hollow shaft 2. To serve this purpose, it is advantageous if the diameter of the casing 12 corresponds at east to the maximum height of the push pin 5, so that the push pin 5 can be withdrawn from the proximal end of the shaft 2 after release of the tool 4.

The illustrated medical instrument 1 is distinguished in general in that it ensures a uniformly strong power transmission independently of the open position of the jaw members, and it is possible to apply this power in controlled degrees so that, after penetration of tough tissue, no uncontrolled breakthrough of the power-impacted jaw members ensues.

| Number Key | |
|---|---|
| 1 | medical instrument |
| 2 | shaft |
| 3 | handle |
| 3a | stationary gripping member |
| 3b | rotatable gripping member |
| 3c | finger loops |
| 3d | pressure surface |
| 4 | tool |
| 4a | rotatable jaw member |
| 4b | stationary jaw member |
| 5 | push pin |
| 5a | contact surface |
| 5b | recess |
| 6 | compensation lever |
| 7 | guide groove |
| 8 | connecting point |
| 9 | rotation point |
| 10 | rotation axis |
| 11 | driving element |
| 12 | casing |
| 12a | recess |

What is claimed is:

1. A medical instrument with a hollow shaft extending along a longitudinal axis, said hollow shaft having at its proximal end a handle consisting of at least two gripping members and at its distal end a tool consisting of at least two jaw members, where at least one of the jaw members of the tool can rotate in relation to the at least one other jaw member of the tool for purposes of opening and closing by means of one rotatably designed gripping member of the handle, and wherein the at least one rotatable jaw member and the gripping member of the handle that serves to rotate the at least one jaw member are connected to one another by means of a push pin stored in the hollow shaft and the push pin can be displaced exclusively in the axial direction by means of the corresponding at least one rotatable gripping member of the handle, wherein at least one of the jaw members is directly mounted to the distal end of the hollow shaft, wherein at least a portion of the push pin is inside, at least partly in form-locking connection, a rigid casing extending along the longitudinal axis, which in turn is inside, at least partly in form-locking connection, the hollow shaft, and wherein the form-locking connection of the push pin and the rigid casing secures the push pin against rotation relative to said rigid casing about the longitudinal axis at least in some sections in the casing.

2. A medical instrument according to claim 1, wherein the rigid casing has a recess for receiving the push pin, wherein the recess has a rectilinear cross-section in a plane substantially perpendicular to the longitudinal axis.

3. A medical instrument according to claim 1, wherein the diameter of the casing corresponds at least to the maximum height of the push pin.

4. A medical instrument according to claim 1, wherein, in order to displace the push pin in the distal direction a pressure surface is configured on the rotatable gripping member for contacting a contact surface of the push pin.

5. A medical instrument according to claim 4, wherein, in order to displace the push pin in the proximal direction a driving element is mounted on the rotatable gripping member, which element engages in a recess configured in the push pin.

6. A medical instrument according to claim 1, wherein the push pin can be removed from the shaft as a unit.

7. A medical instrument with a hollow shaft extending along a longitudinal axis, said hollow shaft having at its proximal end a handle consisting of at least two gripping members and at its distal end a tool consisting of at least two jaw members, where at least one of the jaw members of the tool can rotate in relation to the at least one other jaw member of the tool for purposes of opening and closing by means of one rotatably designed gripping member of the handle, and wherein the at least one rotatable jaw member and the gripping member of the handle that serves to rotate the at least one jaw member are connected to one another by means of a push pin stored in the hollow shaft and the push pin can be displaced exclusively in the axial direction by means of the corresponding at least one rotatable gripping member of the handle, wherein at least a portion of the push pin is inside, at least partly in form-locking connection, a rigid casing extending along the longitudinal axis, which in turn is inside, at least partly in form-locking connection, the hollow shaft, wherein the rigid casing has a recess for receiving the push pin, the recess having a rectilinear cross-section in a plane substantially perpendicular to the longitudinal axis, and wherein the form-locking connection of the push pin and the rigid casing secures the push pin against rotation relative to said rigid casing about the longitudinal axis at least in some sections in the casing.

8. A medical instrument according to claim 7, wherein the casing has a recess of rectilinear cross-section for receiving the push pin, which is rectilinear in cross-section.

9. A medical instrument according to claim 7, wherein the diameter of the casing corresponds at least to the maximum height of the push pin.

10. A medical instrument according to claim 7, wherein, in order to displace the push pin in the distal direction a pressure surface is configured on the rotatable gripping member for contacting a contact surface of the push pin.

11. A medical instrument according to claim 10, wherein, in order to displace the push pin in the proximal direction a driving element is mounted on the rotatable gripping member, which element engages in a recess configured in the push pin.

12. A medical instrument according to claim 7, wherein the push pin can be removed from the shaft as a unit.

* * * * *